United States Patent [19]

Edgar

[11] Patent Number: 4,743,775
[45] Date of Patent: May 10, 1988

[54] ABSORPTION GAUGE FOR DETERMINING THE THICKNESS, MOISTURE CONTENT OR OTHER PARAMETER OF A FILM OF COATING

[75] Inventor: Roger F. Edgar, Maldon, England

[73] Assignee: Infrared Engineering, Ltd., Essex, England

[21] Appl. No.: 915,882

[22] Filed: Oct. 1, 1986

[30] Foreign Application Priority Data

Nov. 19, 1985 [GB] United Kingdom ............... 8528448

[51] Int. Cl.⁴ ..................... G01N 21/86; G01V 9/04
[52] U.S. Cl. .................................. 250/571; 250/560; 250/226
[58] Field of Search .............. 250/562, 563, 571, 572, 250/560, 561, 226; 356/429–431, 443, 444, 381, 382

[56] References Cited

U.S. PATENT DOCUMENTS

| | | | |
|---|---|---|---|
| 3,210,546 | 10/1965 | Perron | 250/563 |
| 3,807,873 | 4/1974 | Nakamori | 356/429 |
| 3,827,808 | 8/1974 | Cho | 250/571 |
| 3,907,440 | 9/1975 | Eichenberger et al. | 356/429 |
| 4,320,967 | 3/1982 | Edgar | 356/429 |

FOREIGN PATENT DOCUMENTS 1382081 1/1975 United Kingdom .

Primary Examiner—David C. Nelms
Assistant Examiner—William L. Oen
Attorney, Agent, or Firm—Mason, Fenwick & Lawrence

[57] ABSTRACT

The apparatus includes means for directing a plurality of beams of radiation of different spectral compositions to a sample such as a film or coating. A part of the beams is transmitted through the sample and received by a radiation detector. Another part of the beams reflected by the sample is in turn reflected, preferably by a concave mirror, back through the sample onto another radiation detector. The signals 'a' and 'b' from the detectors are combined in accordance with the relationship $a/(1-b/a)$ to suppress optical interference effects.

7 Claims, 3 Drawing Sheets

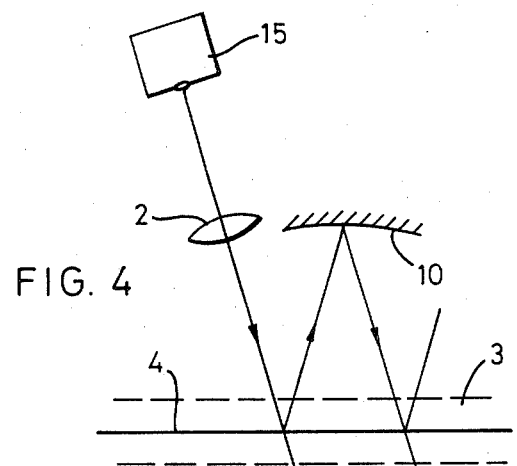
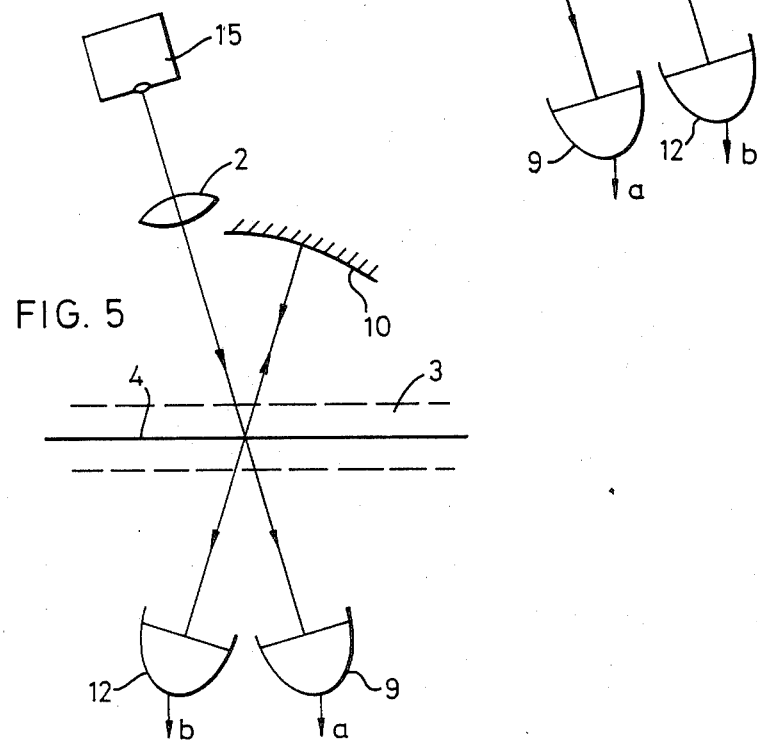

ABSORPTION GAUGE FOR DETERMINING THE THICKNESS, MOISTURE CONTENT OR OTHER PARAMETER OF A FILM OF COATING

This invention relates to an absorption gauge for determining the thickness, moisture content or other parameter of a film or coating capable of transmitting electromagnetic radiation.

U.S. Pat. No. 4,320,967 describes examples of known optical absorption gauging apparatus employing a transmission measurement for the determination of, for example, the thickness or composition of a film or coating, in which optical interference errors are suppressed by the use of additional optical components to ensure that reflected as well as transmitted light co-operates in the measurement.

The technique customarily used in optical absorption gauging apparatus for film or coating measurement comprises the steps of deriving two or more beams of radiation of different spectral composition, causing them to be transmitted through the material to be measured, collecting by optical means some part of the transmitted radiation and causing it to impinge upon a radiation responsive detector or detectors, demodulating or otherwise processing the output signal or signals from said detector or detectors so as to provide a first set of electrical signals respectively representing the separate intensities of the beams of radiation that have been transmitted through the material to be measured, and of computing the parameter or parameters that are to be determined by forming a second set of electrical signals related to ratios of first electrical signals. The spectral compositions of the beams are chosen so as to provide a differential change in the intensities of the beams as a result of their transmission through the material to be measured with respect to the parameter or parameters to be determined. A beam exhibiting a substantial change in the parameter or parameters to be determined may be described as an absorption beam, whilst a beam exhibiting a lesser change may be described as a reference beam.

When an apparatus of this type is used to measure a parameter of a thin film or coating (for example, the thickness, moisture content or composition of said film or coating), the precision of the measurement may be degraded by optical interference effects which cause changes in the transmitted intensities of the beam, these changes being not directly related to the variation in the parameter to be measured.

The strength of these optical interference effects is a function of the spectral composition of the several beams of radiation. It is well known that broadening of the spectral bandwidth of a beam of radiation reduces its propensity to generate optical interference effects. Unfortunately, for measurements on certain thin films, the degree of broadening of spectral bandwidth necessary to reduce optical interference errors to acceptably low levels has the secondary effect of reducing the differential change in the transmitted intensities of the several beams to a level at which photometric errors will degrade the precision of the measurement.

Now it is known in the prior art that optical interference errors in beams reflected from a film or coating are of opposite polarity to those of spectrally similar beams transmitted from the same film or coating, so that a combination of reflected and transmitted beams can greatly reduce the magnitude of optical interference errors. U.K. Pat. No. 1,382,081 discloses the technique of combining either transmitted and reflected beams, or the outputs of detectors responsive thereto, so as to cancel errors in a measured intensity signal due to optical inteference. U.S. Pat. No. 4,320,967 discloses a technique of optically combining transmitted and reflected beams at a diffusing element and feeding their sum to a responsive detector. Whilst the optical arrangements disclosed in U.S. Pat. No. 4,320,967 are relatively straightforward to implement, the technique suffers from a major limitation. Because the reflected beam is re-directed through the film or coating not all of it will be transmitted, but a secondary proportion will be reflected a second time. Even if this secondarily reflected component can be re-directed a further time, a tertiary proportion of it will be reflected a third time and so on. In practice, it is not possible to design a conventional optical system that will continue to present the multiple reflected beams to the film or coating after more than about 3 reflections so that the correction for optical interference effects can never be perfect.

The present invention overcomes this limitation by providing apparatus for determining or controlling a parameter or parameters which represent the thickness, moisture content, composition or other property of a film or coating capable of transmitting radiation, the apparatus including:

(a) means for defining a sample zone in which the sample of the film or coating can be received;

(b) means for deriving a plurality of beams of radiation of differing spectral compositions;

(c) optical directing means for directing a plurality of said beams to said sample whereby a transmitted part of said beams is transmitted by said sample, and a reflected part of said beams is reflected from said sample;

(d) reflector means for reflecting said reflected part of said beams through said sample;

(e) radiation responsive detector means for receiving said transmitted part and said reflected part which has been transmitted through said sample and for providing respective signals which represent said transmitted and reflected parts;

(f) means for processing said signals to provide a first set of electrical signals which are each proportional to a value of intensity theoretically obtainable if said detector means received substantially all of the radiation reflected from said sample onto said reflector means and reflected thereby through said sample onto said detector means, the signals in said first set representing the separate intensities of the beams of different spectral compositions as received by said detector means; and (g) means for providing at least one second signal representing the ratio of at least two of the signals of said first set.

In preferred embodiments of the invention, a first radiation detector receives the transmitted part of said beams and produces a signal 'a' in response thereto; a second radiation detector receives the reflected part of said beams which has been transmitted through said sample and produces a signal 'b' in response thereto; and means for processing signals 'a' and 'b' to provide a resultant signal $a/(1-b/a)$. The resultant signals are processed in order to provide the signals in the first set representing the separate intensities of the beams of different spectral compositions as received by the detector means. Such processing may include the use of demodulating means as is known in the art. Whilst thiis apparatus requires the use of at least two radiation responsive detectors it has the advantage that said radiation responsive detectors can be mounted in proximity on the same side of the film or coating to be measured.

In order to reduce the possibility of error due to optical misalignment, which is particularly important when measurements are made on moving samples (e.g. such as a film produced by a continuous process), the reflecting means is preferably a concave mirror. The concave mirror may be either spherical, or ellipsoidal and it may have an aperture therethrough for transmitting radiation from a source to the sample in the sample zone. Such a mirror is used to re-image the light reflected by the film onto diffusing means located between the detector means and the sample in the sample zone, the diffusing means and the sample being located in conjugate planes. The concave mirror and/or the optical directing means is tilted with respect to the plane of the sample (e.g. a moving film) in the sample zone, so that the reflected part of the beams of radiation are displaced to one side of the transmitted part whereby the reflected and transmitted parts, which have both been transmitted through the sample, can be received by respective independent radiation detectors. These detectors are preferably identical and mounted on a common heat sink to ensure similar tracking sensitivities.

According to one embodiment of the invention, there are provided first and second radiation responsive detector means mounted in proximity; optical filter means for deriving a plurality of beams of radiation of differing spectral compositions from said source; first optical directing means for directing said plurality of beams from said source to said sample zone; second optical directing means for directing a part of each of said plurality of beams, which is transmitted by said sample when present, from said sample zone to said first radiation responsive means; third optical directing means (which includes, or is formed by said reflecting means) for directing a part of each said plurality of beams, with is reflected by said sample when present, from said sample zone back to said sample zone; and fourth optical directing means for directing a part of each of said plurality of beams which is redirected by said third optical directing means and which is transmitted by said sample when present, from said sample zone to said second radiation responsive detector means.

Alternatively, whilst the same optical directing means are used, instead of using optical filter means there are provided emitting diode or laser means for deriving a plurality of beams of radiation of differing spectral compositions.

The second signal or signals may be supplied to indicating means to provide a read-out of the parameter or parameters to be measured, or it or they may be supplied to control means which are operative for example, to maintain said parameter or parameters at a given value.

Whilst reference is made above to four optical directing means, it will be apparent to those skilled in the art that it will commonly be possible to select optical directing means such that the functions of the first and second optical directing means can be effected by a single optical component or set of components and similarly the functions of the third and fourth optical directing means can be effected by a single optical component or set of components.

Preferably a concave mirror can be used to carry out the functions of the third and fourth optical directing means.

Embodiments of the invention are described below with reference to the accompanying drawings in which:

FIG. 4 is a schematic diagram of an apparatus for measuring the thickness, moisture content or other parameter of a film or coating in which the light beams directed towards primary and secondary detectors are approximately parallel and pass through different areas of the sample.

FIG. 5 is a schematic diagram of an apparatus for measuring the thickness, moisture content or other parameter of a film or coating in which the light beams directed towards primary and secondary detectors pass through the same area of the sample.

Hereinafter the term 'light' will be used in place of 'electromagnetic radiation', it being understood that as used 'light' does not imply a restriction to the part of the electromagnetic spectrum to which the eye is sensitive.

Figure 1:
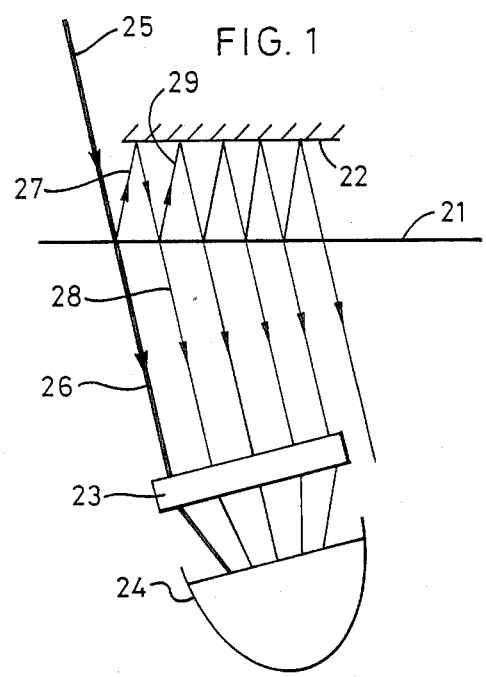
FIG. 1 shows a possible way in which optical interference errors might be suppressed when a beam of light is transmitted through a film or coating.

In FIG. 1 a beam of light 25 impinges upon a sample of a film or coating 21. A portion 26 of beam 25 is transmitted by sample 21 and directed onto radiation responsive detector 24 by optical system 23. A portion 27 of beam 25 is reflected by sample 21 onto reflecting surface 22 which returns it to sample 21.

In turn a portion 28 of portion 27 is transmitted by sample 21 and directed onto radiation responsive detector 24 by optical system 23, and a portion 29 of portion 27 is reflected by sample 21 onto reflecting surface 22 which returns it to sample 21. This sequence will be repeated until it is physically no longer possible for the optical system to collect and direct the multiply reflected light onto the detector 24.

It is apparent that the beam of light 25 must be at an oblique angle to the sample surface and with such a system it will be difficult to collect that portion of the light which has been reflected more than a few times by the sample.

If we represent the fraction of light transmitted by the sample as 't' and the fraction reflected by 'r' we can obtain effective suppression of optical interference by collecting the series of beams falling onto the detector 24. This series is $$t + tr + tr^2 + tr^3 + tr^4 \ldots \text{etcetera.}$$

This may be written $$t(1 + r + r^2 + r^3 + r^4 \ldots),$$

which in turn can be expressed as $$t/(1-r).$$

In practice, to measure t and r directly would require radiation responsive detectors on both sides of the sample. This is possible but not very convenient.

If two detectors are placed in proximity on one side of the sample one can measure the transmission 't' and the other can measure the product 'rt' arising from light which has undergone a single reflection at the sample, followed by transmission. If the detector signals are Sp and Ss respectively, then:

$$T = C\, Sp/(1 - Ss/Sp),$$

where C is a constant.

If 'a' represents the signal from the first detector and 'b' represents the signal from the second then a signal in which optical interference effects have been suppressed is given by $$a/(1-b/a).$$

Figure 2:
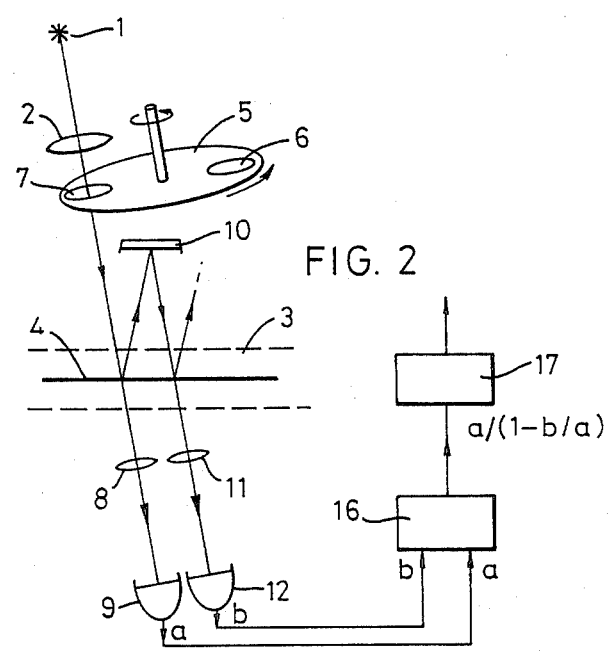
FIG. 2 is a schematic diagram of an apparatus for measuring the thickness, moisture content or other parameter of a film or coating, in which a broadband source of radiation and optical filters are used to derive the plurality of beams of radiation of differing spectral compositions.

This calculation is readily effected by either analogue or digital electronic means. Referring to FIG. 2, light from a source 1 is directed by first optical system 2, into sample zone 3 (in which may be present a sample of film or coating 4), by way of a rotating wheel 5 which carries optical filters 6 and 7. The light selected by optical filters 6 and 7 and transmitted by sample 4 is directed by the second optical system 8 onto the first radiation responsive detector 9. The light selected by optical filters 6 and 7 and reflected by sample 4 is re-directed by third optical system 10 back into sample zone 3. That part of the redirected light which is transmitted by sample 4 is directed by fourth optical system 11 onto second radiation responsive detected 12.

The signal 'a' from the first detector 9 and the signal 'b' from the second detector 12 are supplied to analogue or digital electronic means 16 which calculates the value $a/(1-b/a)$ and produces a resultant signal which represents, or is proportional to this value. The resultant signal is supplied to (known) means 17 for providing a first set of signals representing the respective separate intensities of the beams of different spectral compositions and second signals representing the ratio of at least two signals of the first set of signals. These ratios provide information relating to thickness, moisture content, composition or other property of the film or coating being measured.

The criteria for the selection of optical filters 6 and 7 and the use of more than the two filters shown in FIG. 2 are known in the prior art and will not be discussed further here.

In FIG. 2 the first optical system 2 is conveniently a lens, but a simple aperture can be used instead to define the direction of the beams. The third optical system 10 is conveniently a concave mirror. The second optical system 8 and the fourth optical system can conveniently be lenses and/or diffusing elements. The use of diffusing elements in front of the detectors improves the tolerance of the apparatus to misalignment of its components and to movement of the sample 4 within the sample zone 3.

The optical systems in FIG. 2 are disposed so that the light that is re-directed onto sample 4 by the third optical system 10 and is then reflected a second time by sample 4 will not be permitted to fall upon either of the radiation responsive detectors 9 and 12.

Figure 3:
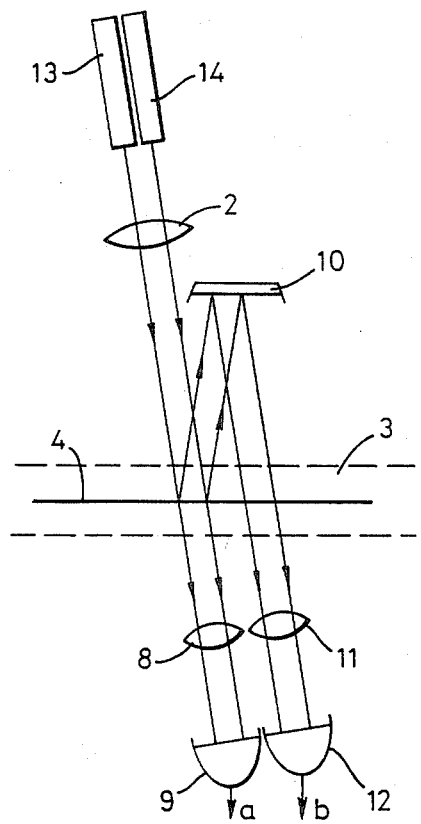
FIG. 3 is a schematic diagram of an apparatus for measuring the thickness, moisture content or other parameter of a film or coating in which radiation emitting diodes are used to derive the plurality of beams of radiation of differing spectral compositions.

Referring to FIG. 3 radiation emitting diodes 13 and 14 are used to generate beams of different spectral composition which are directed by first optical system 2 into sample zone 3 in which may be presented a sample of film or coating 4. The portion of the beams that is transmitted by sample 4 is directed by second optical system 8 onto the first radiation responsive detector 9. The portion of the beams that is reflected by sample 4 is redirected back into sample zone 3 by the third optical system 10. The part of the re-directed beams that is transmitted by sample 4 is directed by the fourth optical system 11 onto the second radiation responsive detector.

Radiation emitting diodes 13 and 4 are capable of being switched on and off at high speed by known electronic techniques and the beams of differing spectral composition can readily be generated in rapid succession by time sequenced switching of the emitting diodes 13 and 14. Save for the means of generating the beams of differing spectral composition, the systems described above with reference to FIGS. 2 and 3 are very similar. The scope of the invention is not restricted to the means of generating beams of differing spectral composition described above but encompasses alternative means known in the art.

Examples of such alternative means include the use of prisms or diffraction gratings to select the wavelength characteristics of the beams from a broadband source such as a filament lamp. Further examples of alternative means include the use of lasers and the use of a single laser whose output radiation is tuneable over a range of wavelengths.

Referring to FIGS. 2 and 3 radiation responsive detectors 9 and 12 need not be matched in sensitivity, but their relative sensitivities should not change. This may be achieved by mounting said detectors onto a common heatsink which may be temperature controlled. Any difference in relative sensitivity between detectors 9 and 12 may be compensated for by adjusting the degree of amplification to which the signals from the detectors are subjected. The electronic means whereby the signals from the detectors are amplified and combined to give signals according to the formula $$a/(1-b/a)$$

where a represents the signal from the first detector and b the signal from the second detector and the subsequent processing of these combined signals, use techniques well known in the prior art and will not be discussed further here.

Referring to FIG. 4, beams of light of spectrally different composition, originating from a source or an assembly of sources 15, are directed by first optical system 2 into sample zone 3 in which may be presented a sample of film or coating 4. The portion of each light beam transmitted by sample 4 falls onto the first radiation responsive detector 9. The portion of each light beam that is reflected by sample 4 is re-directed back into sample zone 3 by concave mirror 10. That part of the re-directed beams that is transmitted by sample 4 falls onto second radiation responsive detector 12.

Concave mirror 10 is designed to image the plane normally occupied by the sample 4 onto the second radiation responsive detector 12. The light directed towards first detector 9 by optical system 2 is approximately parallel with the light directed towards second detector 12 by concave mirror 10.

In the system represented in FIG. 4 there is no need for optical directing means between the sample zone and the radiation responsive detectors, although the tolerance of the system to misalignment will be improved if detectors 9 and 12 are set behind diffusing elements through which the light must pass to reach said detectors.

Referring to FIG. 5, beams of light of spectrally different composition, originating from a source of an assembly of source 15, are directed by first optical system 2 into sample zone 3 in which may be presented a sample of film or coating 4. The portion of each light beam transmitted by sample 4 falls onto the first radiation responsive detector 9. The portion of each light beam that is reflected by sample 4 is re-directed back into sample zone 3 by concave mirror 10. That part of the re-directed beams that is transmitted by sample 4 falls onto second radiation responsive detector 12.

Concave mirror 10 is designed to image the plane normally occupied by the sample 4 onto the second radiation responsive detector 12. The light directed towards the first detector 9 by optical system 2 and the light directed towards the second detector 12 pass through approximately the same area of the sample.

In order to achieve effective suppression of optical interference effects the plane of the sample 4 must be oriented so that its normal bisects the angle between the beams travelling to the detectors 9 and 12.

In the system represented in FIG. 5 there is no need for optical directing means between the sample zone and the radiation responsive detectors although the tolerance of the system to misalignment will be improved if detectors 9 and 12 are set behing diffusing elements through which the light must pass to reach said detectors.

In the embodiments described above with reference to FIGS. 2 to 5 the apparatus has been described utilising configurations in which the beams of different spectral composition are obtained sequentially in time, either by use of filters in a rotating wheel or by switching of sources electronically. It will be clear to persons skilled in the art that the invention is not restricted to optical gauging apparatus in which a radiation responsive detector receives beams of differing spectral composition sequentially in time, but may apply equally to such apparatus in which a radiation responsive detector simultaneously receives beams of differing spectral composition modulated with differing carrier frequencies. Likewise the use of the invention in optical gauging apparatus in which a different radiation responsive detector is used for each of the beams of differing spectral composition may be seen to be straightforward.

Whilst examples of the invention have been described, further changes and modifications may be made without departing from the scope of the invention.

I claim:

1. Apparatus for determining or controlling a parameter or parameters which represent the thickness, moisture content, composition, or other property of a film or coating capable of transmitting radiation, comprising:
    (a) means for defining a sample zone in which a sample of a film or coating can be received;
    (b) means for deriving a plurality of beams of radiation of differing spectral compositions;
    (c) optical directing means for directing a plurality of said beams to said sample whereby said beam is divided by said sample into a transmitted part transmitted by said sample, and a reflected part reflected from said sample;
    (d) reflector means for reflecting said reflected part of said beams through said sample;
    (e) a first radiation detector which receives the transmitted part of said beams and produces a signal "a" in response thereto, and a second radiation detector which receives the reflected part of said beams, reflected only once by said sample, and produces a signal "b" in response thereto;
    (f) processing means for processing said signals "a" and "b" to provide a resultant signal $a/(1-b/a)$ or a signal proportional thereto, said resultant signal being processed in order to provide a first set of electrical signals representing the separate intensities of the beams of different spectral compositions as received by said first and second radiation detectors; and
    (g) means for providing at least one second signal representing the ratio of at least two of the signals of said first set of electrical signals.

2. Apparatus according to claim 1, wherein said reflecting means comprises a concave mirror, the concave mirror and/or the optical directing means being so orientated with respect to a plane in which the sample is received that the reflected part of said beams is displaced to one side of the transmitted part whereby the reflected and transmitted parts, which have both been transmitted through the sample, can be received by the first and second detectors.

3. Apparatus according to claim 2 and further including diffusing means located between said detectors and the sample receiving zone, the diffusing means and the sample receiving plane being located in conjugate planes with respect to the concave mirror.

4. Apparatus according to claim 3, wherein the concave mirror is either spherical or ellipsoidal.

5. Apparatus according to claim 1, wherein the means for deriving a plurality of beams of radiation of differing spectral compositions comprises a source of electromagnetic radiation and optical filter means for deriving a plurality of beams of radiation of differing spectral compositions from said source.

6. Apparatus according to claim 1, wherein said means for deriving a plurality of beams of radiation of differing spectral compositions comprises laser means.

7. Apparatus according to claim 1, wherein said means for deriving a plurality of beams of radiation of differing spectral compositions comprises light emitting diode means.

* * * * *